US005177287A

United States Patent [19]

Sato et al.

[11] Patent Number: 5,177,287

[45] Date of Patent: Jan. 5, 1993

[54] CATALYST COMPOSITION, PROCESS FOR CRACKING NON-AROMATIC HYDROCARBONS AND PROCESS FOR ISOMERIZING $C_8$ AROMATIC HYDROCARBONS

[75] Inventors: Kimihiko Sato; Risuke Suzuki; Hiroshi Horiuchi, all of Matsuyama, Japan

[73] Assignee: Teijin Petrochemical Industries, Ltd., Tokyo, Japan

[21] Appl. No.: 786,072

[22] Filed: Oct. 31, 1991

Related U.S. Application Data

[62] Division of Ser. No. 500,248, Mar. 27, 1990, Pat. No. 5,089,459.

[30] Foreign Application Priority Data

Mar. 29, 1989 [JP] Japan ........ 1-74874

[51] Int. Cl.[5] ........ C07C 5/22

[52] U.S. Cl. ........ 585/481; 585/482; 585/752

[58] Field of Search ........ 585/752, 481, 482

[56] References Cited

U.S. PATENT DOCUMENTS

| | | | |
|---|---|---|---|
| 4,485,185 | 11/1984 | Onodera et al. | 502/71 |
| 4,868,145 | 9/1989 | Dessau et al. | 502/66 |

FOREIGN PATENT DOCUMENTS

| | | |
|---|---|---|
| 320179 | 6/1989 | European Pat. Off. . |
| 361424 | 4/1990 | European Pat. Off. . |
| 2600668 | 12/1987 | France . |
| 2115306A | 9/1983 | United Kingdom . |

*Primary Examiner*—Patrick P. Garvin
*Assistant Examiner*—E. D. Irzinski
*Attorney, Agent, or Firm*—Wenderoth, Lind & Ponack

[57] ABSTRACT

A catalyst composition consisting essentially of (A) a crystalline aluminosilicate zeolite having a silica/alumina mole ratio of at least 10, at least 50% of all its cation sites being occupied by an alkali metal cation (component A), and (B) a refractory inorganic oxide having (b-1) platinum and (b-2) tin and/or indium supported thereon (component B). A process for cracking non-aromatic hydrocarbons in the presence of the catalyst composition, and a process for isomerizing $C_8$ aromatic hydrocarbons, particularly xylenes, by applying the catalyst composition in combination with a conventional isomerization catalyst.

13 Claims, No Drawings

CATALYST COMPOSITION, PROCESS FOR CRACKING NON-AROMATIC HYDROCARBONS AND PROCESS FOR ISOMERIZING $C_8$ AROMATIC HYDROCARBONS

This application is a division of U.S. Ser. No. 07/500,248 filed Mar. 27, 1990, now U.S. Pat. No. 5,089,459.

This invention relates to a novel catalyst composition and its use, and more specifically, to a catalyst comprising a crystalline aluminosilicate zeolite and a specific metal and to its use in the decomposition reaction of non-aromatic hydrocarbons and the isomerization reaction of $C_8$ aromatic hydrocarbons.

More specifically, this invention relates to an industrially advantageous process for isomerization of xylenes comprising subjecting a hydrocarbon feed stock comprising a major amount of a xylene isomeric mixture and a minor amount of non-aromatic hydrocarbons to xylene isomerization reaction, isolating a specific xylene isomer, preferably p-xylene, from the resulting isomerization reaction mixture, and re-cycling the remaining hydrocarbon mixture to the isomerization reaction, in which non-aromatic hydrocarbon components which build up in the step and reduce the efficiency of the isomerization step are removed from the step by efficiently decomposing them while inhibiting a loss of the xylene isomeric mixture in the step, and in spite of the use of the hydrocarbon feed stock containing the above non-aromatic hydrocarbons, the isomerization of xylenes can be carried out continuously over a long period of time.

The demand for xylenes, particularly p-xylene, is increasing in proportion to the increase in the demand for polyester fibers and films. A typical production process for p-xylene comprises a step of separating p-xylene from a $C_8$ aromatic hydrocarbon mixture by a crystallization method or an adsorption method, a step of contacting the remaining hydrocarbon mixture with a catalyst for isomerizing m-xylene and/or o-xylene to p-xylene and converting the xylenes in the remaining hydrocarbon mixture into a xylene isomeric mixture having a composition nearly close to the thermodynamic equilibrium composition, and a step of recycling the isomeric mixture to the step of separating the p-xylene.

In the above process for producing p-xylene, it is required to bring the composition of the xylene isomeric mixture in the isomeric reaction product as close as possible to a thermodynamic equilibrium composition, to inhibit side reactions such as disproportionation and hydrogenolysis reaction which may induce a loss of xylenes, and to change ethylbenzene, which is difficult to separate by a usual distillation because of its close boiling point with xylenes, to a light or heavy boiling component which is easy to distill, and it is industrially very important for increasing the efficiency of the isomerization reaction and for curtailing the cost of the p-xylene production process to meet these requirements.

On the other hand, the $C_8$ aromatic hydrocarbon mixture used heretofore as a raw material has been industrially obtained by separating aromatic hydrocarbon components from a starting oil such as a catalytic reformed oil or a thermally cracked oil by solvent extraction through the sulfolane method, UDEX method or arosolvan method, and then distilling the solvent extract in order to remove non-aromatic hydrocarbons which adversely affect the efficiency of the isomerization reaction. Typically, this mixture consists of 5 to 20% by weight of ethylbenzene, 15 to 25% by weight of p-xylene, 30 to 60% by weight of m-xylene and 15 to 25% by weight of o-xylene.

However, since the above method of producing the $C_8$ aromatic hydrocarbon mixture as a starting material involves the solvent extraction step, the equipment system becomes complex and results in an increase in the cost of the material.

In recent years, various attempts have been made to increase the recovery of aromatic hydrocarbons such as benzene, toluene, and xylenes in reforming petroleum naphtha, and particularly, success in improving a catalyst for inducing cyclodehydrogenation of paraffinic hydrocarbons has made it possible to carry out this cyclodehydrogenation reaction at low pressures under relatively mild conditions, and an aromatic hydrocarbon mixture having a low non-aromatic hydrocarbon content can be obtained.

With this technological background, there was proposed a method of obtaining a $C_8$ aromatic hydrocarbon mixture having a low non-aromatic hydrocarbon content which can be used for the production of xylenes involving only a distillation treatment of a naphtha reformed oil without using the solvent extraction step (Japanese Patent Publication No. 47231/1982). There was also proposed a process for producing a $C_8$ aromatic hydrocarbon mixture having a relatively low content of non-aromatic hydrocarbons, which comprises distilling a naphtha reformed oil and polymerizing olefins which are difficult to remove by distillation treatment alone and become a poisoning substance of a xylene isomerization catalyst, and again distilling the naphtha reformed oil (Japanese Laid-Open Patent Publication No. 181036/1985). The $C_8$ aromatic hydrocarbon mixture obtained by this process usually contains 0.05 to 3% by weight, typically 0.1 to 2% by weight, of non-aromatic hydrocarbons and the composition of the non-aromatic hydrocarbons is usually 70 to 80% by weight of $C_8$–$C_{10}$ paraffins, and 20 to 30% by weight of $C_8$–$C_{10}$ naphthenes.

If such a $C_8$ aromatic hydrocarbon mixture having small amounts of non-aromatic hydrocarbons produced without going through the solvent extraction treatment can be used directly for the isomerization reaction of xylenes, it can be expected to reduce the cost of the starting material, and consequently, this leads to a reduction in the cost of p-xylene product.

However, when p-xylene is produced by isomerization of xylenes by using the $C_8$ aromatic hydrocarbon mixture containing small amounts of non-aromatic hydrocarbons, even through the amount of non-aromatic hydrocarbons in the starting $C_8$ aromatic hydrocarbon mixture is small if this starting $C_8$ aromatic hydrocarbon mixture is recycled for a certain period of time, the non-aromatic hydrocarbons are gradually accumulated in the step, and adversely affect the xylene isomerization reaction. To cope with this, it is necessary to suspend the reaction regularly and replace all of the hydrocarbons in the step by fresh hydrocarbons. This operation is troublesome.

Thus, although a process for producing a $C_8$ aromatic hydrocarbon mixture containing small amounts of non-aromatic hydrocarbon fractions has previously been proposed, a process for producing p-xylene from this hydrocarbon mixture as a starting material has not yet gained commercial acceptance. Such processes have been proposed in U.S. Pat. No. 4,163,028 and Japanese Laid-Open Patent Publication No. 65027/1984.

A producer who already owns an established process for isomerizing xylenes feels it troublesome to change the catalyst and operating conditions. Since the above method requires feeding of non-aromatic hydrocarbon-containing xylenes under very severe conditions over the catalyst, the activity of the catalyst decreases with time and the activity of decomposing non-aromatic hydrocarbon components also decreases. Consequently, these components are accumulated within the recycle system. Hence, the production efficiency of p-xylene is likely to decrease.

Some of the present inventors extensively studied a process for producing a xylene isomer, particularly p-xylene with good efficiency from a $C_8$ aromatic hydrocarbon mixture still containing small amounts of non-aromatic hydrocarbons which is low in cost, without greatly changing the conventional xylene isomerization reaction process. As described in U.S. Pat. No. 4,700,012, the present inventors discovered a cracking catalyst comprising a zeolite selected from zeolites ZSM-5, ZSM-11, ZSM-12, ZSM-34 and ZSM-48 series, at least 20% of its cationic sites being occupied by cations of metals selected from alkali metals and alkaline earth metals, and a refractory irregularly-shaped inorganic oxide having platinum supported thereon.

According to the above conventional method, the efficiency of decomposing non-aromatic hydrocarbons is high, but to efficiently decompose the non-aromatic hydrocarbons sufficiently inhibiting the loss of xylenes which occurs simultaneously, it is necessary to select the temperature and weight hourly space velocity (WHSV) such that they simultaneously satisfy the following relationships.

$$300 \leqq T \leqq 425 \quad \text{(i)}$$

$$5 \leqq V \leqq 200 \quad \text{(ii)}$$

$$\left(\frac{4}{V} - 1.10\right)T - \frac{1000}{V} - 40 \geqq 5 \quad \text{(iii)}$$

$$1.5\,T = 3\,V \leqq 600 \quad \text{(iv)}$$

In the above, T represents the temperature (°C.), and V is the weight hourly space velocity ($hr^{-1}$).

The assignee of the present invention previously applied for on a patent a catalyst composition consisting essentially of (a) a crystalline aluminosilicate zeolite having a silica/alumina mole ratio of at least 10, at least 50% of all its cationic sites being occupied by alkaline earth metal cations (component A), (b) a refractory inorganic oxide having platinum and tin supported therein (component B) and (c) indium (component C), the indium being supported on the zeolite in component A and/or the refractory inorganic oxide in component (B), and a process for isomerizing $C_8$ aromatic hydrocarbons containing non-aromatic hydrocarbons by using this catalyst composition (U.S. patent application Ser. No. 07/413,721 and European Patent Application No. 89117819.6).

It is a first object of this invention to provide a catalyst composition having better activity of decomposing non-aromatic hydrocarbons.

It is a second object of this invention to provide a catalyst composition having an activity of decomposing a small proportion of non-aromatic hydrocarbons contained in $C_8$ aromatic hydrocarbons at a relatively high rate but a very low activity on the loss of the coexisting $C_8$ aromatic hydrocarbons.

It is another object of this invention to provide an industrial process which enables a $C_8$ aromatic hydrocarbon feed stock containing a small proportion of non-aromatic hydrocarbons to be used in the production of a specific xylene, particularly p-xylene, from the $C_8$ aromatic hydrocarbon stock.

It is still another object of this invention to provide a process in which a $C_8$ aromatic hydrocarbon stock containing a relatively small proportion of non-aromatic hydrocarbons can be used at a low cost in the production of xylenes without drastically changing the isomerizing step of a production process now industrially operated.

Another object of this invention is to provide a process in which the above feed stock containing non-aromatic hydrocarbons can be used in the commercial xylene isomerization process without substantially changing the isomerization catalyst.

Another object of this invention is to provide a composite catalyst composition and a catalyst composition structure for carrying out both the isomerization of xylenes and the decomposition of non-aromatic hydrocarbons by using a $C_8$ aromatic hydrocarbon feed stock containing a small proportion of non-aromatic hydrocarbons.

Other objects of this invention will become apparent from the following description.

The present invention will be described in detail hereinbelow.

The objects and advantages of this invention are achieved in accordance with this invention by a catalyst composition consisting essentially of (A) a crystalline aluminosilicate zeolite having a silica/alumina mole ratio of at least 10, at least 50% of all its cation sites being occupied by an alkali metal cation (component A), and (B) a refractory inorganic oxide having (b-1) platinum and (b-2) tin and/or indium supported thereon (component B).

The invention also provides (1) a composite catalyst composition for isomerization of xylenes prepared by mixing the above catalyst composition and a catalyst composition having an ordinary ability to isomerize xylenes, and (2) a catalyst composition structure for the isomerization of xylenes composed of a layer formed from the above catalyst composition and a layer formed from the catalyst composition having an ordinary ability to isomerize xylenes.

According to this invention, there is also provided a process for producing xylenes, which comprises subjecting a hydrocarbon feed stock formed substantially of a major amount of $C_8$ aromatic hydrocarbons and a minor amount of non-aromatic hydrocarbons to xylene isomerization reaction, separating a specific xylene from the resulting isomerization reaction mixture, and recycling the remaining hydrocarbon mixture to the xylene isomerization reaction, wherein the hydrocarbon feed stock fed to the xylene isomerization reaction or the xylene isomerization reaction mixture subjected to the xylene isomerization reaction is contacted with the above catalyst composition in the vapor phase in the presence of hydrogen.

The catalyst composition of the invention, the composite catalyst composition containing it as a constituent component, and the catalyst composition structure, and the use of these compositions as a catalyst now will be described in detail.

[I] Catalyst composition

The catalyst composition of this invention is substantially consists of the following components A and B.

(A) A crystalline aluminosilicate zeolite having a silica/alumina mole ratio of at least 10, at least 50% of all its cation sites being occupied by alkali metal cations (component A), and (B) a refractory inorganic oxide having (b-1) platinum and (b-2) tin and/or indium supported thereon (component B).

The zeolite constituting component A of the catalyst composition is a crystalline aluminosilicate zeolite having a silica/alumina mole ratio at least 10 (which may be referred to simply as "zeolite"). The zeolites preferably have a silica/alumina mole ratio of from about 20 to from about 2,000, particularly from about 30 to about 200.

Such zeolites are known, and preferably are ZSM-series zeolites developed by Mobil Oil Corporation.

(i) Zeolite ZSM-5 (U.S. Pat. No. 3,702,886)

(ii) Zeolite ZSM-11 (U.S. Pat. No. 3,709,979)

(iii) Zeolite ZSM-12 (U.S. Pat. No. 3,832,449)

(iv) Zeolite ZSM-34 (U.S. Pat. No. 4,086,184)

(v) Zeolite ZSM-48 (Japanese Laid-Open Patent Publication No. 149119/1980)

Of these zeolites, zeolite ZSM-5 and zeolite ZSM-11 are preferred, and zeolite ZSM-5 is most preferred.

At least 50%, preferably at least 60%, of the entire cation sites of the zeolite are occupied by alkali metal cations. Example of the alkali metal cations include lithium (Li), sodium (Na), potassium (K), rubidium (Rb) and cesium (Cs) cations, and the lithium cations and sodium cations are preferred. The lithium cations are especially preferred. The alkali metal cations occupying at least 50%, preferably at least 0%, of the entire cation sites of the zeolite may be cations of one metal species or two or more species of the alkali metals.

The cation sites of the zeolite are acidic active sites based on the alumina ($AlO_2^-$) of the constituent components of the zeolites. By using the zeolite in which at least 50% by weight of its entire cation sites are occupied by alkali metal cations, a loss of xylenes owing to undesirable reactions, such as disproportionation reaction, of xylenes in the $C_8$ aromatic hydrocarbon feed stock or in the xylene isomerization reaction mixture can be greatly reduced, and non-aromatic hydrocarbons can be selectively decomposed.

The aforesaid proportion of the entire cation sites of the zeolite used in this invention may be occupied by alkali metal cations. Suitably, at least 70%, preferably at least 80%, of its entire cation sites are occupied by alkali metal cations and hydrogen ions. Cations other than the alkali metal cations are desirably hydrogen ions. Some of them may be alkaline earth metal cations or other metal cations.

Desirably, when the alkali metal cations are lithium cations, 60 to 100%, preferably 70 to 100%, of the entire cation sites of the zeolite are the lithium cations. When they are sodium cations, 60 to 95% of the entire cation sites of the zeolite are desirably sodium cations.

The zeolite having the above alkali metal cations may be easily obtained by subjecting the known zeolites described hereinabove to an ion-exchange treatment with alkali metal ions in accordance with known methods see, for example, Journal of Catalysis, 43, 292-303 (1976), and Journal of Catalysis, 46, 100-108 (1977)].

Examples of alkali metal compounds used for ion-exchange of alkali metal cations include nitrates such as lithium nitrate and sodium nitrate; chlorides such as lithium chloride and sodium chloride, and sulfates such as lithium sulfate and sodium sulfate.

In the refractory inorganic oxide as a carrier for supporting (b-1) platinum and (b-2) tin and/or indium in component B constituting the catalyst composition of this invention, the refractory inorganic oxide carrier may be those carriers which are usually used in solid catalysts. Examples include silica, alumina, silica-alumina, kaolin, silica-magnesia, zirconia and magnesia. Preferably this carrier has a specific surface area of at least 50 $m^2/g$ Alumina, particularly gamma-alumina, is excellent as the refractory inorganic oxide in component (B) of the catalyst composition of this invention.

The amount of (b-1) platinum to be supported on the carrier is generally 0.005 to 5.0% by weight, preferably 0.01 to 2.0% by weight, especially preferably 0.1 to 1.0% by weight, based on the weight of the carrier in order to inhibit the ring hydrogenation or ring decomposition of the xylenes in the $C_8$ aromatic hydrocarbon feed stock or the xylene isomerization reaction mixture to the greatest possible extent and to promote the decomposition reaction of non-aromatic hydrocarbons to components of lower boiling points. It is presumed that the function of platinum supported on the refractory inorganic oxide is to impart the marked activity of converting the non-aromatic hydrocarbons into components of lower boiling points as a synergistic effect of a combination with the function of zeolite as component A.

In the present invention, (b-2) tin and/or indium is supported on the refractory inorganic oxide in addition to the platinum (b-1). The component (b-2) may be indium alone or tin alone, or a mixture of tin and indium. The (b-2) tin and/or indium is believed to function to moderately suppress the ability of platinum copresent in component (B) to dissociate hydrogen and adsorb and consequently to markedly reduce the ring hydrogenation and ring decomposition of the xylenes in the $C_8$ aromatic hydrocarbon feed stock and to promote the decomposition reaction of the non-aromatic hydrocarbons into components of low boiling points. Thus, the amount of each of tin and indium to be supported on the refractory inorganic oxide is 0.1 to 10 atoms, preferably 0.3 to 7 atoms, preferably 0.5 to 5 atoms, per atom of platinum.

It is also presumed that in addition to the above-mentioned function of indium, indium diffuses in the channels of zeolite in component A to poison the acid sites of the zeolite in the catalyst composition of this invention and strengthen the stereoregular effect in the channels of the zeolite, and therefore, indium will at the same time have an effect of reducing disproportionation and transalkylation of the $C_8$ aromatic hydrocarbons, particularly xylenes. It is not yet clear why indium exhibits such an effect. But as a result of using the catalyst composition of this invention containing indium in contact with the hydrocarbon feed stock used in this invention, the yield of xylenes is high and non-aromatic hydrocarbons can be converted into components having lower boiling points with high conversion activity.

The refractory inorganic oxide having supported thereon (b-1) platinum and (b-2) tin and/or indium supported there may be prepared by successively supporting the components on the carrier, or supporting them simultaneously on the carrier. If the above synergistic effect of platinum (b-1) and tin and/or indium (b-2) in component B is considered, the simultaneously depositing method is preferred in which a uniform solution containing a platinum compound and a tin compound and/or an indium compound is impregnated in the refractory inorganic oxide, removing the solvent, and then drying the impregnated solution.

The use of hydrochloric acid in the simultaneously depositing method is preferred because it results in an effective deposition of the supporting components. Specifically, by including hydrochloric acid in a uniform solution containing the supporting components, there can be obtained a component B in which platinum, tin and indium are homogeneously deposited. Chloroplatinic acid and platinum tetramine complex may be used, for example as platinum compounds to be used in the preparation of component B. Examples of the tin compound are soluble salts such as stannous chloride, tin sulfate and tetraalkyl ammonium chlorostannate. Examples of the indium compounds include indium nitrate [$In(NO_3)_3.3H_2O$], indium sulfate [$In_2(SO_4)_3.9H_2O$], indium trichloride [$InCl_3$], ammonium hexafluoroindate $(NH_4)_3[InF_6]$, and ammonium aquapentachloroindate $(NH_4)_2[InCl_5(H_2O)]$.

Water, methanol, acetone, hydrochloric acid, and mixtures of these may be used as a solvent for dissolving compounds of the components to be deposited.

The catalyst composition of this invention is formed substantially from component A and component B. The suitable weight ratio of the two components is from 1:9 to 9:1, preferably from 2:8 to 8:2.

In preparing the catalyst composition of this invention, a powder of component A and a powder of component B are uniformly mixed in the above proportions, and the mixture is pressed and molded into pellets, tablets, etc. according to the purpose for which the resulting catalyst composition is used.

Prior to use, the catalyst composition so prepared is calcined in an atmosphere containing at least 5% of oxygen at a temperature of 200° to 600° C., preferably 250° to 550° C. After the calcined product is filled in a reactor, it is then subjected to a reducing treatment.

It is believed that in the resulting catalyst composition, in its mode of use, platinum and tin in component B are present mostly in the form of a metal, and indium is present in the form of a metal and/or an oxide.

The above catalyst composition of this invention has high activity of decomposing non-aromatic hydrocarbons such as paraffins or naphthenes and converting them into smaller molecules. Accordingly, the catalyst composition of this invention is advantageously used to decompose or crack a starting mixture containing these non-aromatic hydrocarbons.

[II] Process for decomposing non-aromatic hydrocarbons

The catalyst composition of this invention may be used to decompose paraffins and/or naphthenes to obtain paraffins and/or naphthenes having less carbon atoms. Generally, by contacting a starting mixture containing at least 50% by weight, preferably at least 60% by weight, of $C_6$–$C_{11}$ paraffins and/or naphthenes based on non-aromatic hydrocarbons and having a non-aromatic hydrocarbon content of at least 10% by weight, preferably at least 20% by weight, with the above catalyst composition in the vapor phase in the presence of hydrogen atom, the paraffins and/or naphthenes are decomposed to hydrocarbons having not more than 9 carbon atoms, particularly not more than 7 carbon atoms, at a high conversion.

The reaction temperature at this time is about 250° to about 500° C., preferably from about 300° to about 430° C., especially about 350°60 to about 410° C.

The reaction pressure is generally 0 to 25 kg/cm$^2$-G, preferably 0 to 20 kg/cm$^2$-G. It is advantageous to feed the hydrocarbon feed stock at a WHSV (hr$^{-1}$) of 1 to 500, preferably 4 to 100, especially 10 to 40 hr$^{-1}$.

Hydrogen is fed into the hydrocarbon feed stock in a hydrogen/hydrocarbon mole ratio of from 0.1 to 15, preferably from 0.5 to 5.

[III] A process for isomerizing $C_8$ aromatic hydrocarbons

The catalyst composition of this invention has unique activity such that it has high decomposing activity on non-aromatic hydrocarbons while it has very low activity on the disproportionation or transalkylation of $C_8$ aromatic hydrocarbons, particularly xylenes, and also very low activity of hydrogenating rings of xylenes. Accordingly, the catalyst composition of this invention can be advantageously used industrially in a process for producing xylenes by using a $C_8$ aromatic hydrocarbon feed stock containing non-aromatic hydrocarbons at a relatively low material cost. In an existing xylene producing plant where it is difficult, or virtually impossible, to use a $C_8$ aromatic hydrocarbon feed stock containing non-aromatic hydrocarbons, the catalyst composition permits use of the above cheap raw materials.

Thus, there is provided in accordance with this invention a process for producing xylenes which comprises subjecting a hydrocarbon feed stock formed substantially of a major proportion of $C_8$ aromatic hydrocarbons and a minor proportion of non-aromatic hydrocarbons to xylene isomerization reaction, separating a specific xylene isomer from the resulting isomerization reaction mixture, and re-cycling the remaining hydrocarbon mixture to the xylene isomerization reaction; wherein the hydrocarbon feed stock fed to the xylene isomerization reaction, or the xylene isomerization reaction mixture after the xylene isomerization reaction is contacted with the above-specified catalyst composition in the vapor phase in the presence of hydrogen.

According to the process of this invention, by contacting the hydrocarbon feed stock or the xylene isomerization reaction mixture with the catalyst composition, the non-aromatic hydrocarbons in the feed stock or the reaction mixture are decomposed into hydrocarbons having lower boiling points.

The hydrocarbon feed stock which can be used in the process for producing xylenes in accordance with this invention is composed mainly of a mixture of xylene isomers, and a minor amount of 0.02% by weight, preferably 0.05 to 5% by weight, based on the weight of the hydrocarbon feed stock, of non-aromatic hydrocarbons. This hydrocarbon feed stock is produced, for example, by going through a step of extracting non-aromatic hydrocarbons, or a catalytic reforming process in which the catalyst or the operating conditions are improved so as to omit part of the extraction step [see, for example, Oil & Gas Journal, Apr. 5, 1982, pp. 210–214; Hydrocarbon Processing, Nov., 1982, pp. 102–108 Hydrocarbon Processing, Nov., 1970, pp. 127-136; and Ball. Japan. Petro. Inst., 16, 38-42 (1974)].

The composition of the hydrocarbon feed stock varies depending upon the composition of a material for this feed stock or the method of production, and cannot be strictly defined. It contains as non-aromatic hydrocarbons paraffins and naphthenes having a boiling range of 120° to 150° C. and 8 to 10 carbon atoms.

The non-aromatic hydrocarbons generally contain at least 70% by weight, particularly at least 80% by weight, of $C_9$–$C_{10}$ paraffins and naphthenes.

Typical examples of the non-aromatic hydrocarbons include linear paraffins such as octane, nonane and decane, monoalkylparaffins such as methylheptane, methyloctane, methylnonane, ethylhexane, ethylheptane and ethyloctane, dialkylparaffins such as dimethylhexane, dimethylheptane, dimethyloctane, methylethylpentane, methylethylhexane and methylethylheptane; trialkylparaffins such as trimethylhexane, trimethylheptane and dimethylethylpentane, and naphthenes such as trimethylcyclohexanes and ethylmethylcyclohexanes.

By contacting the these non-aromatic hydrocarbons with the catalyst composition of this invention, they can be easily converted at a high conversion into paraffins and naphthenes having not more than 8 carbon atoms, particularly not more than 7 carbon atoms, and can be simply separated by distillation.

The aromatic hydrocarbons in the hydrocarbon feed stock consists substantially of a $C_8$ aromatic hydrocarbon mixture. The $C_8$ aromatic hydrocarbon mixture may contain up to 40% by weight, particularly not more than 20% by weight, based on the hydrocarbon feed stock, of ethylbenzene besides the xylene isomers. It might contain not more than 0.1% by weight, based on the weight of the hydrocarbon feed stock, of $C_9$ aromatic hydrocarbons such as cumene, ethyltoluenes and trimethylbenzenes. The presence of such a trace amount of $C_9$ aromatic hydrocarbons does not affect the practice of the process of this invention, and a hydrocarbon mixture containing such trace amounts of $C_9$ aromatic hydrocarbons may be used in this invention as a hydrocarbon feed stock.

Preferably, the decomposition reaction of the non-aromatic hydrocarbons in the hydrocarbon feed stock in accordance with this invention is carried out in the vapor phase usually in the presence of hydrogen. The reaction temperature of this decomposition reaction is generally 250 to 500 , preferably 270° to 480° C., especially preferably 280° to 450° C.

Advantageously, the feed rate of the starting material to be fed is generally 1 to 500, preferably 4 to 100, more preferably 10 to 40, WHSV ($hr^{-1}$).

On the other hand, the partial pressure of hydrogen should not be strictly limited, and may be varied depending upon the temperature or WHSV used. Conveniently, it is 0 to 25 $Kg/cm^2$-G, preferably 0.5 to 20 $kg/cm^2$-G, more preferably 0.8 to 15 $kg/cm^2$-G.

The feed rate of hydrogen in terms of the mole ratio of hydrogen/hydrocarbon material is generally from 0.1 to 15, preferably from 1 to 10.

The decomposition reaction of non-aromatic hydrocarbon components described above may be carried out on the hydrocarbon feed stock before it is to be subjected to xylene isomerization reaction. Alternatively, the hydrocarbon feed stock is first subjected to xylene isomerization reaction and then the resulting isomerization reaction mixture before separating a specific xylene isomer may be subjected to the decomposition reaction. At times, it may be subjected to the decomposition reaction at the same time as the xylene isomerization.

As specific procedures, the xylene isomerization catalyst composition (to be referred to as the "isomerization catalyst") and the catalyst composition of this invention (to be referred to as the "decomposition catalyst") can be used in the combinations as outlined below.

(i) A single reactor is filled with a composite catalyst composition consisting of the isomerization catalyst and the decomposition catalyst in any desired form, and in this single reactor, isomerization of xylenes and the decomposition of non-aromatic hydrocarbons are carried out at the same time.

(ii) In one reactor, a catalyst composition structure composed of a layer of an isomerization catalyst and a layer, disposed, above or below it, layer of a decomposition catalyst is provided, and isomerization of xylenes and the decomposition of non-aromatic hydrocarbons are carried out successively in the same reactor.

(iii) The isomerization catalyst is filled in one reactor, and the decomposition catalyst is filled in another reactor connected in series to the front or rear of the first reactor. The isomerization of xylenes and the decomposition of non-aromatic hydrocarbons are thus carried out in the separate reactors.

In this method, the decomposition reaction of the non-aromatic hydrocarbons and the isomerization reaction of xylenes may be carried out successively, or as required, intermittently.

Of the above methods (i) to (iii), the method (ii) or (iii) is preferred because in these methods, the $C_8$ aromatic hydrocarbon feed stock containing non-aromatic hydrocarbons can be used in these methods without substantially greatly changing an existing or known xylene isomerization process.

Thus, according to this invention, the following composite catalyst composition and catalyst composition structure may be provided by combining the known xylene isomerization catalyst with the catalyst of this invention.

(a) A composite catalyst composition for the isomerization of xylenes obtained by mixing the catalyst composition of this invention with a known catalyst composition having the ability to isomerize xylenes.

(b) A catalyst composition structure for the isomerization of xylenes which is composed of a layer formed from the catalyst composition of this invention and a layer formed from the catalyst composition having the ability to isomerize xylenes.

The isomerization reaction of xylenes to be combined with the decomposition reaction of non-aromatic hydrocarbons using the catalyst composition of the invention may be a known reaction or a method which has already been commercially practiced. Some examples are shown below.

(1) A method which comprises contacting a mixture of aromatic compounds including ethylbenzene and xylenes with a catalyst including ZSM-5, ZSM-12 or ZSM-21 zeolite in the vapor phase at a temperature of 500° to 1,000° F. (see U.S. Pat. No. 3,856,872).

(2) A method which comprises contacting a xylene-containing material with a catalyst composition containing a zeolite selected from ZSM-5, ZSM-11, ZSM-12, ZSM-23 and ZSM-35, ZSM-38 and ZSM-48 each containing noble metals at a temperature of 260° to 538° C., preferably 427° to 482° C. at a pressure of 50 to 1,000 psig, preferably 100 to 400 psig at a weight hourly space velocity of 1 to 50, preferably 5 to 15 (see U.S. Pat. Nos. 4,312,790 and 4,385,195).

(3) A method which comprises contacting a xylene isomeric mixture with a catalyst composition comprising a zeolite-containing platinum and a second metal (preferably a metal selected from the group consisting of tin, barium, titanium, indium, cadmium and lead) and selected from the group consisting of ZSM-5, ZSM-11, ZSM-12, ZSM-35 and ZSM-38 at a temperature of 250° to 450° C. under a hydrogen partial pressure of 0 to 25 $kg/cm^2$-G at a weight hourly space velocity of 1 to 500 (see U.S. Pat. No. 4,331,822).

The above-given isomerization methods of xylenes are merely examples, and other methods and improved methods of the above-exemplified methods may be used in this invention.

A specific xylene isomer, for example p-xylene, may be isolated from the reaction mixture obtained after isomerization reaction of xylenes by any known methods. Basically, this separation may be performed by the crystallization method described, for example, in Oil & Gas Journal, Sep., 15, 1975, pp. 201–202; Hydrocarbon Processing, Nov., 1985, p. 175, or the adsorption method described, for example, in Ind. Eng. Chem. Prod. Rce. Dev., 18 (4), 263–268 (1979), and Hydrocarbon Processing, Nov., 1985, p. 176.

The remaining hydrocarbon mixture from which a particular xylene isomer has been so separated may be mixed with a fresh hydrocarbon feed stock and can be recycled to the xylene isomerization reactor directly or via a reactor for decomposing non-aromatic hydrocarbons.

The present invention described hereinabove gives the following industrially excellent advantages:

(a) The present invention permits use of a $C_8$ aromatic hydrocarbon mixture containing small amounts of non-aromatic hydrocarbons which is relatively low in cost and can be obtained only by a distillation operation without requiring the operation of removing non-aromatic hydrocarbons by a solvent extracting method which requires a complex apparatus and a complex operation.

(b) Even if the process of this invention is worked over a long period of time, non-aromatic hydrocarbons are not accumulated in the xylene isomerization reaction system, and xylenes can be isomerized efficiently.

(c) Non-aromatic hydrocarbons can be decomposed at a high efficiency, and the loss of $C_8$ aromatic hydrocarbons, particularly xylenes, is very small.

(d) A xylene production process which is commercially practiced can be employed without changing it greatly.

The following examples illustrate the invention more specifically.

REFERENTIAL EXAMPLE 1

Synthesis of $NH_4^+$-type ZSM-5

Zeolite ZSM-5 was synthesized by the method disclosed in Example 1 of U.S. Pat. No. 3,965,207. Specifically, in its synthesis, water glass was used as a silica source; aluminumsulfate, as an alumina source; and tri-n-propylamine and n-propyl bromide, as a source of an organic nitrogen cation. Furthermore, methyl ethyl ketone was added, and they were reacted in an autoclave under certain conditions. The product was filtered, fully washed with water, and dried overnight in an electric dryer. X-ray diffraction analysis led to the identification of the product as ZSM-5. As a result of chemical analysis, the silica/alumina mole ratio of the product was found to be 70.

The cation site of the resulting zeolite was changed from the sodium ion to an ammonium ion. Specifically, 10 ml of a 10% aqueous solution of ammonium chloride was used per gram of the zeolite, and the mixture was kept for 16 hours under reflux. This operation was repeated twice. The product was filtered and washed with water and dried at 100° C. for 16 hours to give $NH_4^+$-type zeolite ZSM-5.

EXAMPLE 1

(1) Synthesis of Li+-type zeolite ZSM-5

$LiNO_3$ (1.58 g) was dissolved in 100 ml of water, and 10 g of $NH_4^+$-type ZSM-5 obtained in Referential Example 1 was added to the aqueous solution. The mixture was maintained under reflux overnight. The product was filtered, and the resulting product was fully washed with water. It was dried further in an electric dryer at 100° C. for 16 hours. The dry powder was found to contain 0.16% of Li as a result of chemical analysis. Hence, 50% of the cation sites of the product based on alumina was occupied by Li.

(2) Preparation of Pt-In-Sn-$Al_2O_3$

One gram of commercial chloroplatinic acid hexahydrate ($H_2PtCl_6.6H_2O$, a reagent grade special class, a product of Wako Pure Chemicals Co., Ltd.) was dissolved in water.

Indium nitrate trihydrate (108.2 mg) and 20.2 mg of stannous chloride dihydrate were precisely weighed into a 50 ml eggplant-shaped flask, and dissolved in 20 ml of water and 2.0 ml of hydrochloric acid. Furthermore, 2.72 ml of an aqueous solution of chloroplatinic acid was added. Five grams of gamma-alumina gel (ACP-1, a product of Catalyst and Chemical Co., Ltd.) was added to the resulting dark reddish orange aqueous solution, and with stirring the mixture was maintained at 50° C. for 5 hours. Then the water was evaporated at 40° C. under reduced pressure by means of a rotary evaporator. Subsequently, the residue was dried in an electric dryer at 100° C. for 16 hours to prepare alumina containing 0.4% of platinum, 0.21% of tin, and 0.7% of indium.

(3) Preparation of Pt-Sn-$Al_2O_3$

Stannous chloride dihydrate (20.2 mg) was precisely weighed in a 50 ml eggplant-shaped flask, and dissolved in 2.0 ml of hydrochloric acid and 20 ml of water. Furthermore, 2.72 ml of an aqueous solution of chloroplatinic acid was added. Five grams of the gamma-aluminum gel was added to the resulting yellow aqueous solution. With stirring, the mixture was maintained at 50° C. for 5 hours. The mixture was then worked up by the same procedure as in section (2) to prepare alumina containing 0.4% of platinum, and 0.21% of tin.

(4) Preparation of Pt-In-$Al_2O_3$

Indium nitrate trihydrate (108.2 mg) was precisely weighed in a 50 ml eggplant-shaped flask, and dissolved in 20 ml of water. Furthermore, 2.72 ml of an aqueous solution of chloroplatinic acid was added. Five grams of the above gamma-alumina gel was added to the resulting yellow aqueous solution, and the mixture was maintained at 50° C. for 5 hours with stirring. Then, the mixture was worked up by the same procedure as in section (2) above to prepare alumina containing 0.4% of platinum and 0.7% of indium.

(5) Preparation of a catalyst for decomposition of non-aromatic hydrocarbons

Equal weights of aluminas containing tin and/or indium obtained in (2), (3) and (4) were each mixed sufficiently with the ZSM-5 zeolite containing Li obtained in (1). The mixtures were each molded to a size of 10 to 20 mesh to obtain a catalyst A, a catalyst B and a catalyst C.

COMPARATIVE EXAMPLE 1

One gram of commercial chloroplatinic acid was dissolved in 50 ml of water. 2.72 ml of this solution was taken in a 50 ml eggplant-shaped flask, and diluted with 20 ml of water. 2.0 ml of hydrochloric acid was added to the aqueous solution, and 5 g of gamma-alumina gel was added. With stirring, the mixture was maintained at 50° C. for 5 hours.

It was then worked up by the same procedure as in section (2) of Example 1 to prepare alumina containing 0.4% of platinum.

An equal weight of the resulting alumina containing platinum was added to each of the $NH_4^+$-type ZSM-5 zeolite obtained in Referential Example 1 and the $Li^+$-type ZSM-5 zeolite obtained in Example 1, (1). After thorough mixing, the resulting mixture was molded to a size of 10–20 mesh. The resulting compositions were designated as a catalyst D and a catalyst E.

EXAMPLE 2

This example shows that the catalysts obtained by this invention show high decomposing activity on non-aromatic hydrocarbons while suppressing losses of xylenes.

Each of the pelletized catalysts A to E (1 g) was filled in a flowing-type atmospheric pressure fixed bed reactor. The temperature was raised to 400° C. under a nitrogen gas stream. At 400° C., the nitrogen gas as replaced by a stream of hydrogen and the catalyst was maintained for 2 hours to reduce platinum. Then, a xylene mixture containing nonane (which is a $C_9$ paraffin) was fed into the reactor. The reaction conditions were: the reaction temperature 400° C.; WHSV 5 $hr^{-1}$ based on the weight of the catalyst; hydrogen/starting mixture (mole ratio) 2.

Table 1 shows the compositions of the products obtained 2 to 4 hours after the feeding of the starting mixture.

Table 1 shows that the catalysts A to C containing tin and/or indium together with platinum maintained high activity of decomposing non-aromatic hydrocarbons while inhibiting a loss of xylene.

TABLE 1

| | Starting material composition (wt. %) | Product composition (wt. %) | | | | |
|---|---|---|---|---|---|---|
| | | Catalyst A | Catalyst B | Catalyst C | Catalyst D | Catalyst E |
| Composition | | | | | | |
| $C_8$ non-aromatic hydrocarbons | 0.02 | 1.88 | 2.13 | 2.19 | 3.12 | 2.04 |
| n-nonane | 1.06 | 0.07 | 0.01 | 0.05 | 0.03 | 0.09 |
| benzene | 0.00 | 2.62 | 3.02 | 2.41 | 5.39 | 2.76 |
| toluene | 1.52 | 1.80 | 2.03 | 1.80 | 2.79 | 2.02 |
| ethylbenzene | 11.88 | 8.21 | 7.70 | 7.85 | 4.04 | 7.74 |
| p-xylene | 8.99 | 19.85 | 20.02 | 20.18 | 20.16 | 19.88 |
| m-xylene | 57.32 | 45.95 | 45.45 | 45.64 | 44.53 | 45.74 |
| o-xylene | 19.09 | 19.22 | 19.21 | 19.35 | 19.10 | 19.33 |
| $C_9$ aromatic hydrocarbons | 0.12 | 0.40 | 0.43 | 0.53 | 0.84 | 0.40 |
| n-nonane decomposition ratio (%) | — | 93.4 | 99.1 | 95.3 | 97.2 | 91.5 |
| Xylene loss (%) | — | 0.44 | 0.84 | 0.27 | 1.89 | 0.53 |

n-nonane decomposition ratio (%) =

$$\frac{\left(\begin{array}{c}\text{Concentration of}\\ \text{n-nonane in the}\\ \text{starting material}\end{array}\right)-\left(\begin{array}{c}\text{Concentration of}\\ \text{n-nonane in}\\ \text{the product}\end{array}\right)}{\left(\begin{array}{c}\text{Concentration of n-nonane}\\ \text{in the starting material}\end{array}\right)}\cdot 100$$

Xylene loss (%) =

$$\frac{\left(\begin{array}{c}\text{Concentration}\\ \text{of xylene}\\ \text{in the feed}\end{array}\right)-\left(\begin{array}{c}\text{Concentration}\\ \text{of xylene in}\\ \text{the product}\end{array}\right)}{\left(\begin{array}{c}\text{Concentration of xylene}\\ \text{in the starting material}\end{array}\right)}\times 100$$

EXAMPLE 3

This Example shows that the catalysts used in the process of this invention are very effective in inhibiting xylene loss reaction based on the hydrogenation reaction.

Each of the catalysts A to E (1.0 g) was filled in a flowing-type atmospheric pressure-fixed bed reactor, and heated to 400° C. in a stream of nitrogen. At 400° C., the nitrogen stream was replaced by hydrogen, and the catalyst was maintained for 2 hours to reduce platinum. Then, the temperature was lowered to 200° C. in a stream of hydrogen. When the catalyst layer was stabilized at this temperature, benzene was fed. The reaction conditions were the reaction temperature of 200° C. and WHSV of 5 $hr^{-1}$. The compositions of the products obtained 0 to 2 hours after the feeding of the starting materials are shown in Table 2.

Table 2 shows that tin and/or indium is very effective for inhibiting the hydrogenations reaction of the benzene ring.

TABLE 2

| Composition | Composition of the starting material (wt. %) | composition of the product (wt. %) Catalyst A | Catalyst B | Catalyst C | Catalyst D | Catalyst E |
|---|---|---|---|---|---|---|
| non-aromatic hydrocarbons | 0.02 | 0.17 | 3.87 | 0.04 | 28.07 | 28.96 |
| benzene | 99.88 | 99.82 | 96.11 | 99.63 | 71.78 | 71.00 |
| toluene | 0.08 | 0.01 | 0.01 | 0.03 | 0.04 | 0.02 |
| $C_8$ aromatic hydrocarbons | 0.02 | 0.03 | 0.01 | 0.30 | 0.12 | 0.02 |
| Amount of non-aromatic hydrocarbons formed (wt. %) | — | 0.15 | 3.85 | 0.02 | 28.05 | 18.94 |

$$\text{Amount of non-aromatic hydrocarbons formed} = \left(\begin{array}{c}\text{Concentration (wt. \%)}\\ \text{of non-aromatic hydro-}\\ \text{carbons in the product}\end{array}\right) - \left(\begin{array}{c}\text{Concentration (wt. \%) of}\\ \text{non-aromatic hydrocarbons}\\ \text{in the starting material}\end{array}\right)$$

EXAMPLE 4

(1) Synthesis of $Li^+$-type zeolite ZSM-5

Ten grams of $LiNO_3$ was dissolved in 100 ml of water. To this solution 10 g of $NH_4^+$-type ZSM-5 obtained in Referential Example 1 was added. The mixture was maintained overnight under reflux, filtered and fully washed with water. This operation was repeated three times. The powder obtained by filtration and water washing was dried for 16 hours in an electric dryer. Chemical analysis showed that the dry powder contained 0.32% of Li. Accordingly, 100% of the cation sites based on alumina were occupied by Li.

(2) Preparation of Pt-In-Sn-$Al_2O_3$

One gram of commercial chloroplatinic acid hexahydrate was dissolved in 50 ml of water.

108.2 mg of indium nitrate trihydrate and 40.4 mg of stannous chloride dihydrate were precisely weighed in a 50 ml eggplant-shaped flask, and dissolved in 2.0 ml of hydrochloric acid and 20 ml of water, and 2.72 ml of the above aqueous chloroplatinic acid solution was added further. Five grams of gamma-alumina gel was added to the resulting dark reddish orange aqueous solution, and with stirring, the mixture was maintained at 50° C. for 5 hours. Water was evaporated under reduced pressure at 40° C. by means of a rotary evaporator. Subsequently, the residue was dried in an electric dryer for 16 hours at 100° C. to give alumina containing 0.4% of platinum, 0.42% of tin and 0.7% of indium.

(3) Preparation of Pt-Sn-$Al_2O_3$ 108.8 mg of stannous chloride hydrate was precisely weighed in a 50 ml eggplant-shaped flask, and dissolved in 2.0 ml of hydrochloric acid and 20 ml of water. Furthermore, 2.72 ml of the above aqueous chloroplatinic acid solution (2.27 ml) was added. Five grams of the gamma-alumina gel was added to the resulting dark reddish orange aqueous solution, and with stirring, the the mixture was maintained at 50° C. for 5 hours. The reaction mixture was worked up by the same procedure as in section (2) above to prepare alumina containing 0.4% of platinum, 1.14% of tin and 4.8 mmoles/g-alumina of hydrochloric acid.

(4) Preparation of Pt-In-$Al_2O_3$ 171 mg of indium nitrate trihydrate was precisely weighed in a 50 ml eggplant-shaped flask. Five grams of the gamma-alumina gel was added to the resulting yellow aqueous solution, and with stirring, the mixture was maintained at 50° C. for 5 hours. Then, the mixture was worked up by the same procedure as in section (2) to prepare alumina containing 0.4% of platinum, 1.17% of indium, and 4.8 millimoles/g of alumina of hydrochloric acid.

(5) Preparation of catalyst for decomposing non-aromatic hydrocarbons

Each of the aluminas containing platinum, tin and/or indium obtained in section (2), (3) and (4) was added in an equal weight of the Li-containing ZSM-5 zeolite obtained in section (1). They were fully mixed, and molded into a size of 10 to 20 mesh. The resulting compositions were designated as catalysts F, G and H.

COMPARATIVE EXAMPLE 2

An equal weight of the alumina containing platinum which was prepared in Comparative Example 1 was added to the $Li^+$-type zeolite ZSM-5 prepared in section (1) of Example 4. They were fully mixed, and then molded to a size of 10 to 20 mesh. The resulting composition was designated as catalyst I.

EXAMPLE 5

This Example shows that by treating a xylene mixture containing non-aromatic hydrocarbons, the non-aromatic hydrocarbons can be decomposed efficiently under mild conditions and the xylene isomerization reaction can be rapidly carried out.

(a) The catalyst F (3.0 g) obtained in Example 4 was calcined at 450° C. in an atmosphere of air for 8 hours, and then filled in a downflow-type pressurized fixed bed reactor. In a stream of $N_2$, it was heated to 400° C., and at 400° C., the $N_2$ stream was replaced by $H_2$, and the catalyst was maintained at this temperature for 2 hours to reduce the metal. Then, under a stream of $H_2$, the temperature was lowered to 390° C. After the catalyst layer was stabilized at the above temperature, a xylene mixture containing non-aromatic hydrocarbons was fed. It was reacted at a reaction temperature of 390° C. under a pressure of 7.4 kg/$cm^2$-G at a WHSV of 30 $hr^{-1}$ with the hydrogen/starting mixture being kept at a mole ratio of 2. The products obtained 118 and 120 hours after feeding the starting mixture were analyzed.

(b) The catalyst G (3.0 g) obtained in Example 4 was filled in a downflow-type pressurized fixed bed reactor, and the pretreatment of the catalyst and the reaction were carried out in the same way as in section (1). The products obtained 56 to 58 hours after the feeding of the starting mixture were analyzed.

(c) The catalyst H (3.0 g) obtained in Example 4 was filled in a downflow-type pressurized fixed bed reactor, and the pretreatment of the catalyst and the reaction of the starting mixture were carried out in the same way as in section (a). The products obtained 68 to 70 hours after the feeding of the starting mixture were analyzed.

(d) The catalyst I (3.0 g) obtained in Example 4 was filled in a downflow-type pressurized fixed bed reactor, and the pretreatment of the catalyst and the reaction of the starting mixture were carried out in the same way as in section (a). The products obtained 76 to 78 hours after the feeding of the starting mixture were analyzed.

The results of (a) to (d) are shown in Table 3. The results given in Table 3 show that the catalyst compositions of this invention can decomposed the non-aromatic hydrocarbons in the mixture while inhibiting a loss of the xylene isomeric mixture.

TABLE 3

| | Catalyst F | | Catalyst G | | Catalyst H | | Catalyst I | |
|---|---|---|---|---|---|---|---|---|
| Reaction conditions | | | | | | | | |
| Temperature (°C.) | 390 | | 390 | | 390 | | 390 | |
| Pressure (kg/cm²-G) | 7.4 | | 7.4 | | 7.4 | | 7.4 | |
| WHSV (hr⁻¹) | 30 | | 30 | | 30 | | 30 | |
| $H_2$/HC (mole ratio) | 2 | | 2 | | 2 | | 2 | |
| | Composition (wt. %) | | Composition (wt. %) | | Composition (wt. %) | | Composition (wt. %) | |
| Component | Starting material | Product | Starting material | Product | Starting material | Product | Starting material | Product |
| $C_8$ non-aromatic hydrocarbons | 0.06 | 0.55 | 0.06 | 0.40 | 0.03 | 1.38 | 0.05 | 2.71 |
| $C_9$ paraffin | 0.99 | 0.71 | 1.01 | 0.74 | 1.04 | 0.62 | 1.02 | 0.45 |
| $C_9$ naphthene | 0.20 | 0.16 | 0.17 | 0.16 | 0.18 | 0.10 | 0.18 | 0.05 |
| benzene | 0.00 | 0.05 | 0.00 | 0.07 | 0.00 | 0.05 | 0.00 | 0.12 |
| toluene | 1.48 | 1.46 | 1.47 | 1.48 | 1.48 | 1.46 | 1.47 | 1.41 |
| ethylbenzene (EB) | 11.84 | 11.75 | 11.85 | 11.26 | 11.73 | 11.39 | 11.84 | 10.91 |
| p-xylene (Px) | 8.90 | 15.19 | 8.90 | 16.29 | 8.90 | 14.47 | 8.90 | 16.98 |
| m-xylene | 57.28 | 50.93 | 57.31 | 49.99 | 57.29 | 51.26 | 57.31 | 48.44 |
| o-xylene | 19.13 | 19.10 | 19.11 | 19.02 | 19.17 | 19.08 | 19.11 | 18.76 |
| $C_9$ aromatic hydrocarbons | 0.12 | 0.10 | 0.12 | 0.09 | 0.18 | 0.19 | 0.12 | 0.17 |
| Non-aromatic hydrocarbon decomposition ratio (%) | | | | | | | | |
| $C_9$ paraffin | 28.8 | | 26.7 | | 40.2 | | 55.9 | |
| $C_9$ naphthene | 21.2 | | 3.6 | | 46.9 | | 71.2 | |
| Px approach to equilibrium (%) | 56.1 | | 65.8 | | 50.4 | | 74.0 | |
| EB decomposition ratio (%) | 0.8 | | 0.8 | | 2.9 | | 7.9 | |
| Xylene loss (%) | 0.12 | | 0.04 | | 0.65 | | 1.34 | |

*Px* approach equilibrium =

$$\frac{\left(\begin{array}{c}\text{Concentration of}\\ \text{p-isomer in the}\\ \text{product xylene}\end{array}\right) - \left(\begin{array}{c}\text{Concentration}\\ \text{of p-isomer in}\\ \text{the xylene of}\\ \text{starting material}\end{array}\right)}{\left(\begin{array}{c}\text{Equivalent}\\ \text{concentration}\\ \text{of p-isomer}\\ \text{at the reaction}\\ \text{temperature}\end{array}\right) - \left(\begin{array}{c}\text{Concentration}\\ \text{of p-isomer in}\\ \text{the xylene of}\\ \text{starting material}\end{array}\right)} \times 100$$

*EB* decomposition ratio =

-continued $$\frac{\left(\begin{array}{c}\text{Concentration}\\ \text{of ethylbenzene}\\ \text{in the starting}\\ \text{material}\end{array}\right) - \left(\begin{array}{c}\text{Concentration}\\ \text{of ethylbenzene}\\ \text{in the product}\end{array}\right)}{\left(\begin{array}{c}\text{Concentration of ethylbenzene}\\ \text{in the starting material}\end{array}\right)} \times 100$$

Decomposition ratio of non-aromatic hydrocarbons =

$$\frac{\left(\begin{array}{c}\text{Concentration}\\ \text{of non-aromatic}\\ \text{hydrocarbons}\\ \text{in the starting}\\ \text{material}\end{array}\right) - \left(\begin{array}{c}\text{Concentration of}\\ \text{the non-aromatic}\\ \text{hydrocarbons in}\\ \text{the product}\end{array}\right)}{\left(\begin{array}{c}\text{Concentration of non-aromatic hydro-}\\ \text{carbons in the starting material}\end{array}\right)} \times 100$$

REFERENTIAL EXAMPLE 2

Preparation of a xylene isomerization catalyst

Barium chloride ($BaCl_2$; 23.6 g) was dissolved in 200 ml of water. Ten grams of the $NH_4^+$-type ZSM-5 obtained in Referential Example 1 was added to the solution, and under reflux, ion-exchange was carried out for 6 hours. This operation was repeated once, and filtration and thorough washing with water was carried out. The product was dried for 8 hours at 200° C. in an electric dryer, and then calcined for 8 hours in an electric muffle furnace at 450° C. to give $Ba^{2+}$-type ZSM-5.

1.0 g of commercial chloroplatinic acid hexahydrate was dissolved in 50 ml of water. Water (20 ml) was added to 0.68 ml of the above aqueous solution (0.68 ml), and 5 g of the $Ba^{2+}$-type ZSM-5 was suspended. The suspension was maintained at 70° C. for 6 hours. By using a rotary evaporator, the solvent was evaporated at 40° C. The residue was dried at 200° C. for 8 hours by using an electric dryer, and further calcined for 8 hours at 450° C. in an electric muffle furnace under air current to give Pt/Ba.ZSM-5. This zeolite contained 0.1% by weight of platinum and 1.1% by weight of Ba.

An equal weight of gamma-aluminum (a product of Wako Pure Chemicals Co., Ltd.) was added to the resulting catalyst composition, and after thorough mixing, the mixture was molded to a size of 10 to 20 mesh. The resulting composition was designated as catalyst J.

EXAMPLE 6

This Example shows that by treating a xylene mixture containing non-aromatic hydrocarbons, the non-aromatic hydrocarbons can be decomposed efficiently under mild conditions and the xylene isomerization reaction can be rapidly carried out.

(a) 3.0 g of the catalyst J obtained in Referential Example 2 was calcined at 450° C. in an air atmosphere for 8 hours, and then filled in a pressurized fixed bed reactor of the downflow type. It was heated to 400° C. in a stream of $N_2$, and at 400° C., the $N_2$ atmosphere was replaced by $H_2$, and the catalyst was maintained in this state for 2 hours to reduce the metal. Then, under an atmosphere of $H_2$, the temperature was lowered to 390° C. When the catalyst layer was stabilized at this temperature, a xylene mixture containing non-aromatic hydrocarbons was fed, and reacted at a reaction temperature 390° C. under a pressure of 7.4 kg/cm$^2$-G at a WHSV of 10 hr$^{-1}$ with the hydrogen/starting mixture being adjusted to a mole ratio of 2. The products obtained 96 to 104 hours after the feeding of the starting mixture were analyzed.

(b) 3.0 g of the xylene isomerization catalyst J obtained in Referential Example 2 was filled in a downflow-type pressurized fixed bed reactor (catalyst layer II). Then, the catalyst F for decomposition of non-aromatic hydrocarbons obtained in Example 4 was filled in an amount of 1.0 g (catalyst layer I) on top of the catalyst layer II.

The same pretreatment as in (a) above was carried out, and then a xylene mixture containing non-aromatic hydrocarbons was fed, and reacted at a reaction temperature of 390° C. under a pressure of 7.4 kg/cm$^2$-G at a WHSV of 10 hr$^{-1}$ (catalyst layer II) and 30 hr$^{-1}$ (catalyst layer I) with the hydrogen/starting mixture being adjusted to a mole ratio of 2. The products obtained 96 to 104 hours after the feeding of the starting mixture were analyzed.

(c) 3.0 g of the xylene isomerization catalyst J obtained in Referential Example 2 was filled in a downflow-type pressurized fixed bed reactor (catalyst layer II), and then, 1.0 g of the catalyst G obtained in Example 4 was filled on top of this layer (catalyst layer I).

The same pre-treatment and reaction were carried out as in section (b). The products obtained 72 to 80 hours after the feeding of the starting mixture were analyzed.

(d) 3.0 g of the xylene isomerization catalyst J obtained in Referential Example 2 was filled in a downflow-type pressurized fixed bed reactor (catalyst layer II), and then, 1.0 g of the catalyst H obtained in Example 4 was filled on top of this layer (catalyst layer I).

The same pre-treatment and reaction were carried out as in section (b). The products obtained 72 to 80 hours after the feeding of the starting mixture were analyzed.

(e) 3.0 g of the xylene isomerization catalyst J obtained in Referential Example 2 was filled in a downflow-type pressurized fixed bed reactor (catalyst layer II), and then, 1.0 g of the catalyst I obtained in Comparative Example 2 was filled on top of this layer (catalyst layer I).

The same pre-treatment and reaction were carried out as in section (b). The products obtained 72 to 80 hours after the feeding of the starting mixture were analyzed.

The results in (a) to (e) are shown in Table 4 below. The results given in Table 4 show that by using the catalyst of the invention in combination with an existing isomerization catalyst, the non-aromatic hydrocarbons in the starting mixture can be decomposed without affecting the isomerization efficiency.

TABLE 4

| Catalyst layer I<br>Catalyst layer II | Catalyst J | | Catalyst F<br>Catalyst J | | Catalyst G<br>Catalyst J | | Catalyst H<br>Catalyst J | | Catalyst I<br>Catalyst J | |
|---|---|---|---|---|---|---|---|---|---|---|
| Reaction conditions | | | | | | | | | | |
| Temperature (°C.) | 390 | | 390 | | 390 | | 390 | | 390 | |
| Pressure (kg/cm$^2$-G) | 7.4 | | 7.4 | | 7.4 | | 7.4 | | 7.4 | |
| WHSV 2 (hr$^{-1}$) | 10 | | 10 | | 10 | | 10 | | 10 | |
| WHSV 1 (hr$^{-1}$) | — | | 30 | | 30 | | 30 | | 30 | |
| $H_2$/HC (mole ratio) | 2 | | 2 | | 2 | | 2 | | 2 | |
| | Composition (wt. %) | | Composition (wt. %) | | Composition (wt. %) | | Composition (wt. %) | | Composition (wt. %) | |
| Component | Feed | Product | Feed | Product | Feed | Product | Feed | Product | Feed | Product |
| $C_8$ non-aromatic hydrocarbons | 0.05 | 0.79 | 0.07 | 1.28 | 0.05 | 1.10 | 0.05 | 1.33 | 0.05 | 3.36 |
| $C_9$ paraffin | 1.03 | 0.84 | 0.99 | 0.57 | 1.03 | 0.54 | 1.03 | 0.43 | 1.02 | 0.45 |
| $C_9$ naphthene | 0.19 | 0.18 | 0.19 | 0.16 | 0.19 | 0.17 | 0.19 | 0.09 | 0.18 | 0.05 |
| benzene | 0.00 | 2.05 | 0.00 | 2.06 | 0.00 | 2.12 | 0.00 | 2.26 | 0.00 | 2.12 |
| toluene | 1.30 | 1.48 | 1.49 | 1.67 | 1.30 | 1.49 | 1.30 | 1.70 | 1.47 | 1.60 |
| ethylbenzene (EB) | 12.07 | 8.77 | 11.86 | 8.64 | 12.07 | 8.67 | 12.07 | 8.44 | 11.84 | 7.71 |
| p-xylene (Px) | 8.82 | 20.43 | 8.81 | 20.33 | 8.82 | 20.42 | 8.82 | 20.29 | 8.90 | 20.14 |
| m-xylene | 57.35 | 45.01 | 57.13 | 44.91 | 57.35 | 44.99 | 57.35 | 44.69 | 57.31 | 44.50 |
| o-xylene | 19.03 | 19.26 | 18.97 | 19.15 | 19.03 | 19.25 | 19.03 | 19.12 | 19.11 | 18.90 |
| $C_9$ aromatic hydrocarbons | 0.16 | 1.19 | 0.49 | 1.23 | 0.16 | 1.21 | 0.16 | 1.65 | 0.12 | 1.17 |
| Non-aromatic hydrocarbon decomposition ratio (%) | | | | | | | | | | |
| $C_9$ paraffin | 18.4 | | 42.4 | | 45.1 | | 58.4 | | 55.6 | |

TABLE 4-continued

| Catalyst layer I<br>Catalyst layer II | Catalyst J | Catalyst F<br>Catalyst J | Catalyst G<br>Catalyst J | Catalyst H<br>Catalyst J | Catalyst I<br>Catalyst J |
|---|---|---|---|---|---|
| $C_8$ naphthene | 5.3 | 15.8 | 8.9 | 51.7 | 70.7 |
| Px approach to equilibrium (%) | 104.2 | 104.0 | 104.2 | 104.2 | 103.9 |
| EB decomposition ratio (%) | 27.3 | 27.2 | 28.2 | 30.1 | 34.9 |
| Xylene loss (%) | 0.59 | 0.61 | 0.63 | 1.25 | 2.09 |

EXAMPLE 7

In this Example, a catalyst was prepared in the same way as in Example 4, section (2) except that hydrochloric acid was not used.

One gram of commercial chloroplatinic acid hexahydrate was dissolved in 50 ml of water.

108.2 mg of indium nitrate trihydrate and 40.4 mg of stannous dicloride dihydride were precisely weighed in a 50 ml eggplant-shaped flask, and suspended in 20 ml of water. Furthermore, 2.72 ml of the above aqueous chloroplatinic acid solution was added. Five grams of gamma-alumina gel (ACP-1) was added to the resulting dark reddish orange aqueous solution. The mixture was kept at 50° C. for 5 hours with stirring. Then, by using a rotary evaporator, water was evaporated under reduced pressure at 40° C. Subsequently, the residue was dried in an electric dryer at 100° C. for 16 hours to give alumina containing 0.4% of platinum, 0.42% of tin and 0.7% of indium.

An equal weight of the above alumina was added and well mixed with the $Li^+$ zeolite ZSM-5 obtained in Example 4, (1). The mixture was molded to a size of 10 to 20 mesh to give a catalyst K. 3.0 g of the xylene isomerization catalyst J obtained in Referential Example 2 was filled in a downflow-type pressurized fixed bed reactor (catalyst layer II), and then 1.0 g of the catalyst K was filled on top of it (catalyst layer I).

The same pre-treatment and reaction as in Example 5, (b) were carried out. The products obtained 72 to 80 hours after the feeding of the starting mixture were analyzed. The results are shown in Table 5.

EXAMPLE 8

In this Example, catalyst compositions were prepared by varying the mixing ratio of zeolite/alumina at the time of molding, and the activities of these catalysts were examined.

To the $Li^+$-type zeolite ZSM-5 obtained in Example 4, section (1) was added twice amount of the alumina prepared in Example 4, section (2). They were thoroughly mixed, and the mixture was molded to a size of 10 to 20 mesh. The resulting catalyst was designated as catalyst L.

3.0 g of the xylene isomerization catalyst J obtained in Referential Example 2 was filled in a downflow-type pressurized fixed bed reactor (catalyst layer II), and then 1.0 g of the catalyst L was filled on top of it (catalyst layer I).

The same pre-treatment and reaction as in Example 5, (b) were carried out, and the products obtained 72 to 80 hours after the feeding of the starting mixture were analyzed. The results are shown in Table 5.

EXAMPLE 9

In this Example, the activity of the catalyst composition of this invention in which 50% of the cation sites was occupied by lithium was examined.

An equal amount of the alumina prepared in Example 4, (2) was fully mixed with the Li-containing ZSM-5 in which 50% of the cation sites based on alumina was occupied by Li, obtained in Example 1, (1), and the mixture was molded to a size of 10 to 20 mesh to give a catalyst M.

3.0 g of the xylene isomerization catalyst J obtained in Referential Example 2 was filled in a downflow-type pressurized fixed bed reactor (catalyst layer II), and then on top of this layer 1.0 g of the catalyst M was filled (catalyst layer I).

The same pre-treatment and reaction of the starting mixture were carried out as in Example 5, (b). The products obtained 72 to 80 hours after the feeding of the starting mixture were examined. The results are shown in Table 5.

EXAMPLE 10

In this Example, the activity of the catalyst composition in which 60% of the cation sites of zeolite are occupied by sodium was examined. The $NH_4^+$-type zeolite ZSM-5 was treated with 10 ml per gram of the ZSM-5 of a 10% aqueous solution of sodium nitrate under reflux for 16 hours. Then, after filtration and washing with water, the product was dried at 100° C. for 16 hours to give $Na^+$-type zeolite ZSM-5. Chemical analysis showed that the dry powder contained 0.63% of sodium. Accordingly, 60% of the cation sites based on alumina were occupied by sodium.

An equal weight of the alumina prepared in Example 4, (2) was added to the above $Na^+$-type zeolite ZSM-5, and after thorough mixing, the mixture was molded to a size of 10 to 20 mesh. The resulting composition was designated as catalyst N.

3.0 g of the xylene isomerization catalyst J obtained in Referential Example 2 was filled in a down-flow-type pressurized fixed bed reactor (catalyst layer II), and then on top of it, 1.0 g of the catalyst M was filled (catalyst layer I).

The same pre-treatment of the catalyst and reaction of the starting mixture as in Example 5, (b) were carried out. The products obtained 72 to 80 hours after the feeding of the starting mixture were analyzed. The results are given in Table 5.

TABLE 5

| Catalyst layer I<br>Catalyst layer II | Example 7<br>Catalyst K<br>Catalyst J | Example 8<br>Catalyst L<br>Catalyst J | Example 9<br>Catalyst M<br>Catalyst J | Example 10<br>Catalyst N<br>Catalyst J |
|---|---|---|---|---|
| Reaction conditions | | | | |

TABLE 5-continued

| Catalyst layer I / Catalyst layer II | Example 7 Catalyst K / Catalyst J | | Example 8 Catalyst L / Catalyst J | | Example 9 Catalyst M / Catalyst J | | Example 10 Catalyst N / Catalyst J | |
|---|---|---|---|---|---|---|---|---|
| Temperature (°C.) | 390 | | 390 | | 390 | | 390 | |
| Pressure ($kg/cm^2$-G) | 7.4 | | 7.4 | | 7.4 | | 7.4 | |
| WHSV 2 ($hr^{-1}$) | 10 | | 10 | | 10 | | 10 | |
| WHSV 1 ($hr^{-1}$) | 30 | | 30 | | 30 | | 30 | |
| $H_2$/HC (mole ratio) | 2 | | 2 | | 2 | | 2 | |
| | Composition (wt. %) | | Composition (wt. %) | | Composition (wt. %) | | Composition (wt. %) | |
| Component | Feed | Product | Feed | Product | Feed | Product | Feed | Product |
| $C_8$ non-aromatic hydrocarbons | 0.04 | 1.10 | 0.04 | 0.97 | 0.03 | 1.45 | 0.04 | 1.69 |
| $C_9$ paraffin | 1.02 | 0.57 | 1.02 | 0.67 | 0.89 | 0.34 | 1.02 | 0.30 |
| $C_9$ naphthene | 0.20 | 0.16 | 0.20 | 0.18 | 0.16 | 0.12 | 0.20 | 0.13 |
| benzene | 0.01 | 2.14 | 0.01 | 2.13 | 0.00 | 3.15 | 0.01 | 3.26 |
| toluene | 1.47 | 1.66 | 1.47 | 1.65 | 1.48 | 1.75 | 1.47 | 1.75 |
| ethylbenzene (EB) | 11.82 | 8.47 | 11.82 | 8.42 | 11.76 | 6.78 | 11.82 | 6.70 |
| p-xylene (Px) | 8.90 | 20.44 | 8.90 | 20.46 | 8.93 | 20.42 | 8.90 | 20.37 |
| m-xylene | 57.26 | 45.03 | 57.26 | 45.08 | 57.38 | 44.99 | 57.26 | 44.88 |
| o-xylene | 19.19 | 19.26 | 19.19 | 19.28 | 19.20 | 19.25 | 19.19 | 19.20 |
| $C_9$ aromatic hydrocarbons | 0.09 | 1.19 | 0.09 | 1.16 | 0.17 | 1.75 | 0.09 | 1.72 |
| Non-aromatic hydrocarbon decomposition ratio (%) | | | | | | | | |
| $C_9$ paraffin | 44.1 | | 34.3 | | 61.8 | | 70.6 | |
| $C_9$ naphthene | 20.0 | | 10.0 | | 25.0 | | 35.0 | |
| Px approach to equilibrium (%) | 104.0 | | 104.0 | | 104.3 | | 104.0 | |
| EB decomposition ratio (%) | 28.3 | | 28.8 | | 42.3 | | 43.3 | |
| Xylene loss (%) | 0.73 | | 0.62 | | 0.99 | | 1.05 | |

REFERENTIAL EXAMPLE 3

This Referential Example shows a method of preparation of a catalyst composition in which the cation sites of zeolite are occupied by strontium.

Strontium nitrate [$Sr(NO_3)_2$] 10 g was dissolved in 100 ml of water, and to the solution was added 10 g of $NH_4^+$-ZSM-5 obtained in Referential Example 1, and under reflux, ion-exchange was carried out for 5 hours. This operation was repeated three times, and then the product was filtered and washed with water. The ion-exchanged product was dried at 200° C. for 8 hours in an electric dryer, and then calcined at 450° C. for 8 hours in an electric muffle furnace to give Sr-ZSM-5 which contained 1.40% by weight of $Sr^{2+}$. In this zeolite, 67% of the cation sites based on alumina were occupied by strontium cations.

By using 31.2 mg of indium nitrate trihydrate, 40.4 mg of stannous chloride dihydrate, 2.0 ml of hydrochloric acid, 20 ml of water and 5 g of gamma-alumina gel (ACP-1), alumina containing 0.2% of platinum, 0.2% of indium and 0.42% of tin was prepared by the same procedure as in Example 1, section (2).

Equal weights of Sr-ZSM-5 and Pt-In-Sn-$Al_2O_3$ were thoroughly mixed, and molded to a size of 10 to 20 mesh. This composition was designated as catalyst P.

EXAMPLE 11

In this Example, the difference in activity between the catalyst P obtained in Referential Example 3 and the catalyst of the invention (catalyst F) was examined.

The catalyst P obtained in Referential Example 3 was subjected to the same pre-treatment as in Example 6, (a). The results are shown in Table 6 in comparison with the results obtained by using the catalyst F. Table 6 shows that the activity of catalyst F to decompose non-aromatic hydrocarbons was not inferior to the catalyst P, and with the catalyst F, a loss of $C_8$-aromatic hydrocarbons was inhibited in comparison with the catalyst P.

TABLE 6

| Catalyst layer I / Catalyst layer II | Catalyst F / — | | Catalyst P / — | | Catalyst F / Catalyst J | | Catalyst P / Catalyst J | |
|---|---|---|---|---|---|---|---|---|
| Reaction conditions | | | | | | | | |
| Temperature (°C.) | 390 | | 390 | | 390 | | 390 | |
| Pressure ($kg/cm^2$-G) | 7.4 | | 7.4 | | 7.4 | | 7.4 | |
| WHSV 2 ($hr^{-1}$) | | | | | 10 | | 10 | |
| WHSV 1 ($hr^{-1}$) | 30 | | 30 | | 30 | | 30 | |
| $H_2$/HC (mole ratio) | 2 | | 2 | | 2 | | 2 | |
| | Composition (wt. %) | | Composition (wt. %) | | Composition (wt. %) | | Composition (wt. %) | |
| Component | Feed | Product | Feed | Product | Feed | Product | Feed | Product |
| $C_8$ non-aromatic hydrocarbons | 0.06 | 0.30 | 0.05 | 0.70 | 0.07 | 1.28 | 0.05 | 1.88 |
| $C_9$ paraffin | 0.99 | 0.75 | 1.07 | 0.85 | 0.99 | 0.57 | 1.07 | 0.65 |
| $C_9$ naphthene | 0.20 | 0.18 | 0.21 | 0.19 | 0.19 | 0.16 | 0.21 | 0.18 |
| benzene | 0.00 | 0.00 | 0.00 | 0.89 | 0.00 | 2.06 | 0.00 | 2.82 |
| toluene | 1.48 | 1.49 | 1.47 | 1.41 | 1.49 | 1.67 | 1.47 | 1.68 |

TABLE 6-continued

| Catalyst layer I<br>Catalyst layer II | Catalyst F<br>— | | Catalyst P<br>— | | Catalyst F<br>Catalyst J | | Catalyst P<br>Catalyst J | |
|---|---|---|---|---|---|---|---|---|
| ethylbenzene (EB) | 11.84 | 11.83 | 11.88 | 10.43 | 11.86 | 8.64 | 11.88 | 7.18 |
| p-xylene (Px) | 8.90 | 15.17 | 8.77 | 18.82 | 8.81 | 20.33 | 8.77 | 20.40 |
| m-xylene | 57.28 | 51.04 | 57.53 | 47.29 | 57.13 | 44.91 | 57.53 | 44.94 |
| o-xylene | 19.13 | 19.10 | 18.91 | 18.97 | 18.97 | 19.15 | 18.91 | 19.23 |
| $C_9$ aromatic hydrocarbons | 0.12 | 0.14 | 0.11 | 0.45 | 0.49 | 1.23 | 0.11 | 1.04 |
| Non-aromatic hydrocarbon decomposition ratio (%) | | | | | | | | |
| $C_9$ paraffin | 24.2 | | 21.0 | | 42.4 | | 39.3 | |
| $C_9$ naphthene | 10.0 | | 9.5 | | 15.8 | | 14.3 | |
| Px approach to equilibrium (%) | 56.0 | | 89.1 | | 104.0 | | 104.2 | |
| EB decomposition ratio (%) | 0.1 | | 12.2 | | 27.2 | | 39.6 | |
| Xylene loss (%) | 0.02 | | 0.15 | | 0.61 | | 0.75 | |

EXAMPLE 12

This example shows that in preparing a catalyst composition from the catalyst composition of this invention for decomposing non-aromatic hydrocarbons and an existing xylene isomerization catalyst, the method of forming the catalysts does not substantially results in a difference in activity.

(a) The catalyst F obtained in Example 4, (5) and the catalyst J obtained in Referential Example 2 were thoroughly mixed in a weight ratio of 1:3. The resulting catalyst composition was designated as catalyst Q.

(b) 1.5 g of the catalyst J obtained in Referential Example 2 was filled in a flowing-type atmospheric pressure fixed bed reactor (catalyst layer II), and then on top of it, 0.5 g of the catalyst F obtained in Example 4, (5) was filled (catalyst layer I). The catalyst layers were heated to 400° C. under an atmosphere of nitrogen, and at 400° C., the nitrogen atmosphere was replaced by an atmosphere of hydrogen, and the catalyst layer were maintained at this temperature for 2 hours to reduce platinum. Then, the temperature was elevated to 410° C. under an atmosphere of hydrogen, and a xylene mixture containing non-aromatic hydrocarbons was fed into the reactor, and reacted at a reaction temperature of 410° C. and a WHSV of 7.5 $hr^{-1}$ both based on the weight of both catalyst layers I and II with the hydrogen/starting mixture being adjusted to a mole ratio of 2. The products obtained 25 to 27 hours after the feeding of the starting mixture were analyzed.

(c) The catalyst Q (2.0 g) obtained in (a) was filled in a flowing-type atmospheric pressure fixed bed reactor, and the same pre-treatment and reaction as in (b) were carried out. The products obtained 25 to 27 hours after the feeding of starting mixture were analyzed.

The results obtained are shown in Table 7. Table 7 shows that in the activity of decomposing non-aromatic hydrocarbons and the xylene isomerization activity, there is substantially no difference between two-layered composition of catalyst F and catalyst J and the catalyst Q (a mixture of catalysts F and J).

TABLE 7

| Catalyst layer I<br>Catalyst layer II | Catalyst F<br>Catalyst J | Catalyst P<br>— |
|---|---|---|
| Reaction conditions | | |
| Temperature (°C.) | 410 | 410 |
| Pressure ($kg/cm^2$-G) | 0 | 0 |
| WHSV ($hr^{-1}$) | 7.5 | 7.5 |

TABLE 7-continued

| Catalyst layer I<br>Catalyst layer II | Catalyst F<br>Catalyst J | | Catalyst P<br>— | |
|---|---|---|---|---|
| $H_2$/HC (mole ratio) | 2 | | 2 | |
| | Composition (wt. %) | | Composition (wt. %) | |
| Component | Feed | Product | Feed | Product |
| $C_8$ non-aromatic hydrocarbons | 0.04 | 0.82 | 0.04 | 0.80 |
| $C_9$ paraffin | 1.06 | 0.47 | 1.06 | 0.48 |
| $C_9$ naphthene | 0.21 | 0.10 | 0.21 | 0.11 |
| benzene | 0.00 | 0.76 | 0.00 | 0.80 |
| toluene | 1.49 | 1.53 | 1.49 | 1.54 |
| ethylbenzene (EB) | 11.81 | 10.70 | 11.81 | 10.69 |
| p-xylene (Px) | 8.94 | 19.08 | 8.94 | 19.24 |
| m-xylene | 57.14 | 46.95 | 57.14 | 46.78 |
| o-xylene | 19.20 | 19.21 | 19.20 | 19.22 |
| $C_9$ aromatic hydrocarbons | 0.11 | 0.38 | 0.11 | 0.34 |
| Non-aromatic hydrocarbon decomposition ratio (%) | | | | |
| $C_9$ paraffin | 44.3 | | 45.3 | |
| $C_9$ naphthene | 47.6 | | 52.4 | |
| Px approach to equilibrium (%) | 91.5 | | 93.0 | |
| EB decomposition ratio (%) | 9.4 | | 9.5 | |
| Xylene loss (%) | 0.05 | | 0.05 | |

We claim:

1. A process for decomposing non-aromatic hydrocarbons, which comprises contacting a hydrocarbon feed stock containing non-aromatic hydrocarbons with a catalyst composition in the gaseous phase in the presence of hydrogen, wherein the catalyst composition consists essentially of (A) a crystalline aluminosilicate zeolite having a silica/alumina mole ratio of at least 10, at least 50% of all its cation sites being occupied by an alkali metal cation, and (B) a refractory inorganic oxide having (b-1) platinum and (b-2) tin and/or indium supported thereon.

2. The process of claim 1, in which the non-aromatic hydrocarbons have 8 to 11 carbon atoms.

3. The process of claim 2, in which the hydrocarbon feed stock is formed of non-aromatic hydrocarbons and $C_8$ aromatic hydrocarbons.

4. The process of claim 3, in which the hydrocarbon feed stock contains 0.05 to 10% by weight of non-aromatic hydrocarbons.

5. The process of claim 1 in which the hydrocarbon feed stock is formed of non-aromatic hydrocarbons and $C_8$ aromatic hydrocarbons.

6. The process of claim 1 in which the hydrocarbon feed stock contains 0.05 to 10% by weight of non-aromatic hydrocarbons.

7. The processor of claim 2 in which the hydrocarbon feed stock contains 0.05 to 10% by weight of non-aromatic hydrocarbons.

8. A process for producing xylenes, which comprises subjecting a hydrocarbon feed stock formed substantially of a major amount of C8 aromatic hydrocarbons and a minor amount of non-aromatic hydrocarbons to xylene isomerization reaction in which the feed stock is contacted with a catalyst composition containing a zeolite selected from the group consisting of ZSM-5, ZSM-11, ZSM-12, ZSM-21, ZSM-23, ZSM-35, ZSM-38 and ZSM-48, and having the ability to isomerize xylenes, separating a specific xylene from the resulting isomerization reaction mixture, and recycling the remaining hydrocarbon mixtures to the xylene isomerization reaction, wherein the hydrocarbon feed stock fed to the xylene isomerization reaction or the xylene isomerization reaction mixture is subjected to the xylene isomerization reaction is contacted in the vapor phase in the presence of hydrogen with a catalyst composition which consists essentially of (A) a crystalline aluminosilicate zeolite having a silica/alumina mole ratio of at least 10, at least 50% of all its cation sites being occupied by an alkali metal cation, and (B) a refractory inorganic oxide having (b-1) platinum and (b-2) tin and/or indium supported thereon.

9. The process of claim 8 in which said contacting is carried out at a temperature of 250° to 500° C.

10. The process of claim 8 in which said contacting is carried out at a temperature of 270° to 480° C.

11. The process of claim 8 in which the hydrocarbon feed stock is contacted with the catalyst composition at a weight hourly space velocity (WHSV) of 1 to 500.

12. The process of claim 8 in which said contacting is carried out under a pressure of 0 to 25 $kg/cm^2$-gauge.

13. The process of claim 8 in which said contacting is carried out under a mole ratio of hydrogen to the hydrocarbon feed stock of 0.1 to 15.

* * * * *